United States Patent
Hanning et al.

(10) Patent No.: US 6,661,510 B1
(45) Date of Patent: Dec. 9, 2003

(54) DEVICE FOR DETECTION OF FLUORESCENT SPECIES

(75) Inventors: Anders Hanning, Sollentuna (SE); Johan Roeraade, Tumba (SE)

(73) Assignees: Hanning Instruments AB, Sollentuna (SE); R&B Scientific AB, Tumba (SE)

( * ) Notice: Subject to any disclaimer, the term of this patent is extended or adjusted under 35 U.S.C. 154(b) by 0 days.

(21) Appl. No.: 09/743,511

(22) PCT Filed: Jul. 15, 1999

(86) PCT No.: PCT/SE99/01278

§ 371 (c)(1),
(2), (4) Date: Jan. 11, 2001

(87) PCT Pub. No.: WO00/04371

PCT Pub. Date: Jan. 27, 2000

(30) Foreign Application Priority Data

Jul. 16, 1998 (SE) .................................................. 980255

(51) Int. Cl.[7] .............................. G01J 3/30; G01N 21/64
(52) U.S. Cl. ........................ 356/318; 356/317; 356/344; 250/458.1
(58) Field of Search ................................ 204/450–453, 204/455, 556, 603; 356/344, 317–318; 385/125, 12; 250/458.1–461.2

(56) References Cited

U.S. PATENT DOCUMENTS

| | | | | |
|---|---|---|---|---|
| 3,740,113 A | * | 6/1973 | Cass ............................ | 385/125 |
| 3,894,788 A | * | 7/1975 | Gambling et al. ........... | 385/125 |
| 4,477,186 A | | 10/1984 | Carlson | |
| 5,274,240 A | | 12/1993 | Mathies et al. | |
| 5,439,578 A | | 8/1995 | Dovichi et al. | |
| 5,475,487 A | * | 12/1995 | Mariella et al. ............. | 356/338 |
| 5,498,324 A | * | 3/1996 | Yeung et al. ................ | 204/452 |
| 5,567,294 A | | 10/1996 | Dovichi et al. | |
| 5,570,447 A | * | 10/1996 | Liu ............................. | 385/125 |
| 5,604,587 A | * | 2/1997 | Che et al. .................... | 356/246 |
| 5,741,411 A | | 4/1998 | Yeung et al. | |
| 5,741,412 A | | 4/1998 | Dovichi et al. | |
| 5,759,374 A | | 6/1998 | Takahashi et al. | |
| RE36,157 E | * | 3/1999 | Robbins et al. ............. | 385/125 |

FOREIGN PATENT DOCUMENTS

| | | | | |
|---|---|---|---|---|
| DE | 0 723 149 | * | 7/1996 | ......... G01N/27/447 |
| EP | 0 793 098 A1 | | 9/1997 | |
| JP | 10-19846 | | 1/1998 | |
| WO | WO 94/17207 | | 8/1994 | |
| WO | WO 99/39192 | | 8/1999 | |
| WO | WO 00/16085 | | 3/2000 | |
| WO | WO 00/16087 | | 3/2000 | |
| WO | WO 00/160086 | | 3/2000 | |

OTHER PUBLICATIONS

Ju, Jingyue, et al., "Design and Synthesis of Fluorescence Energy Transfer Dye–Labeled Primers and Their Application for DNA Sequencing and Analysis." Analytical Biochemistry 231, 131–140 (1995).

(List continued on next page.)

Primary Examiner—F. L. Evans
Assistant Examiner—Kara Geisel
(74) Attorney, Agent, or Firm—Gary M. Nath; Todd L. Juneau; Joshua B. Goldberg

(57) ABSTRACT

A device for detection of one or several fluorescent species, said species being contained in a medium, said medium being contained in a conduit, said device comprising a means of exciting the fluorescent species by light, said medium and conduit making up a structure that is transparent to the exciting and the emitted fluorescent light, and said device comprising one or several such structures, may be improved by letting at least part of the emitted fluorescent light be guided away from the illumination zone by total internal reflection (TIR) in said structure and collected from one end of said structure.

30 Claims, 10 Drawing Sheets

OTHER PUBLICATIONS

Swerdlow, Norman, et al., "Three DNA Sequencing Methods Using Capillary Gel Electrophoresis and Laser–Induced Fluorescence." Analytical Chemistry 63, 2835–2841 (1991).

Chen, Da Yong, et al., "Low–cost, high–sensitivity laserinduced fluorescence detection for DNA sequencing by capillary gel electrophoresis." Journal of Chromatograhpy 559, 237–249 (1991).

Ueno, Kyoji, et al., "Simultaneous Monitoring of DNA Fragments Separated by Electrophoresis in a Multiplexed Array of 100 Capillaries." Analytical Chemistry 66, 1424–1431 (1994).

Carrilho, Emanuel, et al., "Factors to be considered for robust high–throughput automated dna sequencing using a multiple–capillary array instrument." Proceedings of the Society of Photo–Optical Instrumentation Engineers 2985, 4–18 (1997).

Anazawa, Takashi, et al., "A Capillary Array Gel Electrophoresis System Using Multiple Laser Focusing for DNA Sequencing." Analytical Chemistry 68, 2699–2704 (1996).

Kheterpal, Indu, et al., "DNA sequencing using a four–color confocal fluorescence capillary array scanner." Electrophoresis 17, 1852–1859 (1996).

Takahashi, Satoshi, et al., "Multiple Sheath–Flow Gel Capillary–Array Electrophoresis for Multicolor Fluorescent DNA Detection." Analytical Chemistry 66 1021–1026 (1994).

Quesada, Mark A., et al., "Multiple capillary DNA sequencer that uses fiber–optic illumination and detection." Electrophoresis 17, 1841–1851 (1996).

Dasgupta, Purnendu K., "Luminescence Detection with a Liquid Core Waveguide". Analytical Chemistry, vol. 71, No. 7, pp. 1400–1407, Apr. 1, 1999.

* cited by examiner

A

B

DEVICE FOR DETECTION OF FLUORESCENT SPECIES

The present invention relates to an improvement in the kind of devices that are being used for detection of fluorescent species.

Fluorescence detection or fluorometry is a well established and often used method within analytical chemistry. The main features of fluorescence detection are high selectivity and very high sensitivity, and the method is often applied to detection of trace constituents in samples of various kinds. Fluorescence detectors consist, in general, of three main subsystems, i/ an excitation light source and associated optics, ii/ a sample cell, and iii/ collection optics and light detector. The light source generates the light that excites the fluorescent species. The most often used light sources are high intensity lamps, like, e.g., xenon lamps or lasers. The excitation optics transports the light from the light source to the illumination zone, where the light excites the sample. Focusing optics is most often used, but also fiber optics and other kinds of waveguides, for example, may be used. When a laser light source is used, the focusing optics may, in some cases, be omitted. The sample can contain one or several fluorescent species. The sample is, in general, present in a medium, e.g., a liquid solution, which in turn is contained in some kind of sample cell. The sample cell may, e.g., be a compartment into which the sample is first loaded, then detected while being. stationary, and finally withdrawn. The cell may also be part of some kind of conduit, through which the sample is transported to and from the illumination zone. The collection optics collects the emitted fluorescent light in an efficient way, and transports it to the light detector. Also for the collection optics, focusing elements are commonly used, but also, e.g., fiber optics may be used. The collection, as well as the excitation, optics may also comprise some kind of device, e.g., a monochromator or one or several filters, for selection or dispersion of wavelengths. The excitation is most often performed at one wavelength or a few well-defined wavelengths, or, alternatively, the excitation wavelength may be scanned. The detection may be performed at one or several discrete wavelengths or wavelength intervals, or scanned or dispersed over a wavelength interval, or the total amount of emitted light may be detected. Wavelength selective detection increases the versatility and selectivity of fluorometry, and is a prerequisite in applications like, e.g., four colour DNA sequencing. There are many different kinds of light detectors, e.g., photodiodes, diode arrays, CTD:s (charge transfer devices, including CCD:s (charge coupled devices) and CID:s (charge injection devices)), and photomultiplier tubes.

One of the most common and most important uses of fluorometry is as a detection method in connection with analytical methods wherein the sample is contained and transported in some kind of conduit. Such analytical methods include, but are not limited to, CE (capillary electrophoresis), LC (liquid chromatography), and FIA (flow injection analysis). In this context, the present invention will mainly be discussed in connection with CE, but applications to other analytical methods are obvious to the skilled person. CE is a well-established separation method with the possibility to analyse very small amounts of sample, and yielding a very high separation efficiency.

Fluorescence detection, and especially LIF (laser induced fluorescence), is a well-established detection technique for CE. Lasers have two main advantages: i/ the high intensity of the light, and ii/ the ability to focus the laser beam to a small spot within the capillary. It is important that the size of the light beam at the point of excitation does not contribute to band broadening: the width of CE peaks may require beam diameters of 100 $\mu$m or less. In the most common, and well-established, optical set-up, the orthogonal set-up, the capillary is illuminated with a laser, and the emitted light is collected at 90° to the direction of the laser beam. The main concerns, in order to maximise the sensitivity, are to maximise the light collection efficiency, and to minimise the amount of stray light reaching the light detector. High collection efficiency is, in general, obtained by using high numerical aperture collection optics. The term stray light is used here to denote all kinds of unwanted, detected light. Stray light may, to some extent, be rejected through the use of spectral and/or spatial filters. Electrophoresis capillaries are often protected by a polymer coating, e.g., polyimide, which has to be removed before fluorescence detection can be performed. Scattering of primary laser light may occur if there are polymer or other particles left on the capillary wall, if the wall is scratched, or if there are heterogeneities within the wall or the medium inside the capillary. Further, light scattering occurs at every optical interface according to Fresnel's laws of reflection. In particular, the cylindrical columns ordinarily used in CE pose a problem, since they scatter light also at 90° to the direction of the laser beam. Also, most materials scatter light by elastic (Rayleigh) Raman molecular scattering. Scattered primary light may often, but not in all cases, be efficiently rejected by spectral filtering or wavelength dispersion. Wavelength shifted secondary light may present a more severe problem. Inelastic (Stokes shifted) Raman scattering or fluorescence emission from polymer or dirt particles on the column wall, from the column wall itself, from the medium in which the sample is contained, or from impurities in the medium or in the sample itself may not be easily rejected by spectral filtering or wavelength dispersion. Spatial filtering may be obtained by, e.g., shallow focal depth collection optics and apertures. The light collection is spatially concentrated to the region of the medium, while light emanating from other regions is rejected.

For high efficiency separation methods, utilizing small diameter columns and small samples, and yielding very narrow analyte bands at the detector, like e.g., micro-LC and, in particular, CE, it is imperative that the detection is performed on column and that the detection volume is as small as possible. Use of an external detection cell with diameter larger than the column will lead to band broadening, and coupling to such a cell does, in general, cause dead volumes leading to further band broadening. The maximum allowable detection volume for, e.g., a highly efficient CE separation on a 100 $\mu$m column may be on the order of or less than 2 nl.

One proposed device for maximising light collection efficiency and minimising stray light is the confocal fluorescence microscope [Ju, J. et al., Anal. Biochem. 1995, 231, 131–40]. A laser beam is reflected by a low-pass dichroic beam splitter, and focused by a microscope objective to a very small spot, on the order of 10 $\mu$m, inside the capillary. The emitted fluorescent light is collected by the same objective, but transmitted through the beam splitter to the detection optics. By focusing the collection optics tightly inside the capillary, stray light contributions from the capillary wall are diminished. By placing an aperture at the focal point of the collected fluorescent light, stray light may be further rejected by spatial filtering. High light collection efficiency is achieved by using a high numerical aperture microscope objective. Drawbacks of this device include the need for very strict mechanical tolerances, very careful optical alignment, and the sensitivity to, e.g., vibrations. These drawbacks are a consequence of the shallow focal depth utilized. Further, for cylindrical capillaries, the problem of focusing light and light collection in the interior of a body lacking circular symmetry is encountered.

Another proposed device for optimisation of detection sensitivity is the sheath flow cell [Swerdlow, H. et al., Anal. Chem. 1991, 63, 2835–41; Chen, D. Y. et al., J. Chromatogr. 1991, 559, 237–46]. The analyte to be detected is eluted from the capillary, and excited immediately outside the end of the capillary in a stream of buffer flowing through a high purity quartz cuvette. Since the analyte is detected post-capillary, stray light contributions from the capillary wall are omitted. Further, since the quartz cuvette may be designed with flat optical surfaces, the light scattering problem associated with curved surfaces is omitted. High light collection efficiency is achieved by using high numerical aperture collection optics. The use of this device demands very careful control of flow conditions and flow impedances in order to maintain the integrity of the analyte stream. Further, the presence of particles, bubbles, or impurities in the sheath flow buffer may lead to large amounts of stray light.

In order to increase the sample throughput of CE analysis, like, e.g., for large scale DNA sequencing, it is desirable to run CE in a multitude of capillaries simultaneously. Such multiplexed analysis brings about several additional optical and geometrical problems with regard to fluorescence detection. Most often, the multitude of capillaries are arranged side-by-side in a parallel fashion, so that the array of capillaries form a planar array at the detection point.

The conventional on-column orthogonal set-up may be applied to capillary array detection [Ueno, K. et al., Anal. Chem. 1994, 66, 1424–31; Carrilho, E. et al., Proceedings of the Society of Photo-Optical Instrumentation Engineers 1997, 2985, 4–18]. However, problems with illumination are encountered. If the planar array of capillaries is illuminated by, e.g., a number of parallel laser beams or a line-focused laser beam, the exciting light may form a plane that is orthogonal to the plane of the capillary array. With this geometry, there is no orthogonal direction left for the collection of light. A 90° angle between exciting and emitted light may be obtained by tilting the array of capillaries, but such designs lead to the generation of excessive stray light as well as problems with light collection efficiency. As an alternative, the capillary array may be illuminated by one single laser beam in the same plane as the array, which laser beam hits the different capillaries in a subsequent manner [Anazawa, T. et al., Anal. Chem. 1996, 68, 2699–2704; Yeung, E. S. et al., U.S. Pat. No. 5,741,411, 1998]. With this design, the collection optics may be placed at 90° to the incoming beam. However, since the incoming beam will hit a multitude of optical interfaces, a lot of stray light is generated. Additionally, since some laser power is lost at each interface, the available laser power will rapidly drop as the laser beam travels through the multitude of capillaries, leading to a decreased fluorescence signal. Further, since laser beams are divergent, it is not possible to keep a tight focus over an extended distance of the beam. The result is that some capillaries will be illuminated by a not so tightly focused beam, which may cause detection band broadening and loss of separation resolution of the electrophoretic peaks.

The principle of the confocal microscope may also be applied to capillary array detection [Mathies, R. A. et al., U.S. Pat. No. 5,274,240, 1993; Kheterpal, I. et al., Electrophoresis, 1996, 17, 1852–59]. In this case, the focused laser beam has to be scanned over the capillary array (or vice versa). Thus, it is necessary to use moving parts in the detector, which is not desirable, especially in view of the demanded tight mechanical tolerances and the susceptibility to vibrations. Further, since the laser power is shared in time between all the different capillaries, the duty cycle per capillary is low, which decreases the total light collection efficiency per capillary. These problems are particularly pronounced when using large arrays of capillaries.

Also the sheath flow cell [Takahashi, S. et al., Anal. Chem. 1994, 66, 1021–26; Dovichi, N. J. et al., U.S. Pat. No. 5,567,294, 1996; Dovichi, N. J. et al., U.S. Pat. No. 5,741,412, 1998; Takahashi, S. et al., U.S. Pat. No. 5,759,374, 1998] may be applied to capillary array detection. However, specific drawbacks are encountered. Again, the simple orthogonal setups discussed above can not be used. One possibility is to illuminate the planar array of analyte streams orthogonally with a plane of light (e.g., a line focused laser beam), and collect the emitted light in the same plane as the capillary array, i.e., end-on collection with respect to the capillaries. However, fundamental optical constraints limit the efficient collection of light from an extended line of objects (i.e., the capillary ends). In order to decrease the longest dimension of the array of capillary ends, an alternative is to arrange the capillaries in a three dimensional array, i.e., in a bundle, but then the laser beam will interact with the samples over an extended distance, which may lead to divergence, loss of focus, and detection band broadening. Also, tight bundling of many capillaries may result in band broadening due to inefficient dissipation of Joule heat. Further, sheath flow detection in connection with capillary arrays put extreme demands on the sophistication, control, and tolerances of the flow system.

A multicapillary DNA sequencing device based on transverse illumination and guiding of the emitted fluorescent light by total internal reflection (TIR) in the capillaries has also been proposed [Takubo, K., JP Patent No. 10019846, 1998]. However, no optical coating on the capillaries was proposed, so TIR conditions will not be fulfilled. Since the refractive index (RI) of the gel inside the capillaries in most practical cases will be approximately equal to the RI of the electrolyte buffer, into which the capillary ends are immersed, most of the light will escape radially through the circumference of the capillaries, and will not reach the capillary ends. Also, bundling of capillaries without optical coating will give rise to severe optical crosstalk between the capillaries, again preventing most of the light from reaching the end of the capillary in which it was emitted. Further, bundling of capillaries all the way from the injection end to the detection point will give rise to substantial Joule heating, impairing the electrophoretic resolution.

Fiber optics may also be used to transport the exciting light and collect the emitted light [Quesada, M. A. et al., Electrophoresis, 1996, 17, 1841–51]. However, alignment of a large number of individual fibers and capillaries involves a huge amount of work. Further, the amount of stray light may be expected to exceed that of the confocal scanner or the sheath flow cell.

The present invention is based on the idea that a device for detection of one or several fluorescent species, said species being contained in a medium, said medium being contained in a conduit, said device comprising a means of exciting the fluorescent species by light, said medium and conduit making up a structure that is transparent to the exciting and the emitted fluorescent light, and said device comprising one or several such structures, may be improved by letting at least part of the emitted fluorescent light be guided away from the illumination zone by total internal reflection (TIR) in said structure and collected from one end of said structure.

Such a device offers simplicity and robustness with respect to mechanics, optics, and liquid handling, as well as high light collection efficiency, low stray light, and easy adaptability to capillary array detection.

For light travelling in a material with refractive index $n_1$ and striking the surface of a material with refractive index $n_2$ at an angle $\alpha$ to the normal to the surface, TIR occurs if $$n_1 \sin \alpha > n_2$$

Thus, $n_1$ has to be larger than $n_2$. Under conditions of TIR, all of the light is, in principle, reflected back into the first material. Fore reflection at angles smaller than $\alpha$, some of the light is reflected and some is transmitted.

Thus, in one aspect, the present invention provides a device characterized in that the distance between the illumination zone and the light collection end of said structure is large enough to allow light rays emanating from the illumination zone, which do not fulfil the conditions for TIR, to be efficiently transmitted out of the light guiding part of said structure before reaching the light collection end. Such a device ensures that only light guided by TIR through the structure will be collected and detected at the end of the structure. By using a suitable arrangement, most of the exciting, primary light and part of the stray light can be forced not to fulfil the conditions for TIR, and to be transmitted out of the light guiding structure before reaching the light collection end.

In another aspect, the present invention provides a device that is characterized in that the distance between the illumination zone and the light collection end of said structure is at least four times, or preferably at least eight times, or even more preferably at least sixteen times, larger than the largest cross sectional dimension of the light guiding part of said structure. If said distance is four times larger, most of the light that reaches the light collection end will have been subject to at least one reflection event. However, since the rejection of light that is not subject to TIR is more efficient upon multiple reflection events, the values eight or sixteen are more favourable.

Further, if the illumination takes place in the immediate vicinity of the light collection end, scattering and diffraction of the primary exciting light due to edge effects may cause increased levels of stray light. Even, e.g., a well-focused laser beam has a finite extent, and such effects may occur close to sharp edges. The present invention provides for a means of avoiding such effects.

The expression "species" is use to denote any fluorescent entity, such as molecules, ions, supra-molecular aggregates, micelles, particles, or whole cells or parts of cells. The expression "medium" is used to denote a liquid of high or low viscosity, a semi-rigid gel, or a solid material. The expression "conduit" is used to denote any elongated entity physically containing said medium, in which entity said species may be transported, such as, but not limited to, a tube, a capillary, a column, or a channel formed in, e.g., glass, quartz, silicon, or an organic polymer. In one particular case, the conduit is a separation column for CE or LC. Said medium may or may not be transported within said conduit. The exciting light may be within the ultraviolet, visible, near-infrared or infrared range. The expression "structure" is used to denote any entity comprising and physically defining said conduit and said medium. The term "light guiding part of the structure" denotes that part of the structure that is actually guiding the light, and may refer to the medium, the conduit, or the medium and the conduit. The expression "transparent" means that the material must be able to transmit light with low loss, i.e., not highly absorbing and not highly scattering at the relevant wavelengths. The "light collection end of the structure" is that end where the guided light rays leave the structure and may be collected and detected by optical means. This mode of light collection excludes the decoupling of light from the structure by means of any external optical decoupler before reaching the end of the structure. An example of such a decoupler may be an optical fiber pigtailed onto the structure. In one particular case, the light collection end is one end of a separation column for CE or LC. The "illumination zone" is the location where the exciting, primary light interacts with the structure and excites the fluorescent species.

The advantages of the invention will be better understood from the following discussion of the beneficial influence of different aspects and embodiments of the invention. Clarifying examples will mainly refer to detection in connection with CE, but, as will be apparent to the skilled person, the invention is not limited to such detection.

Reference is being made to the accompanying drawings, wherein.

Figure 1:
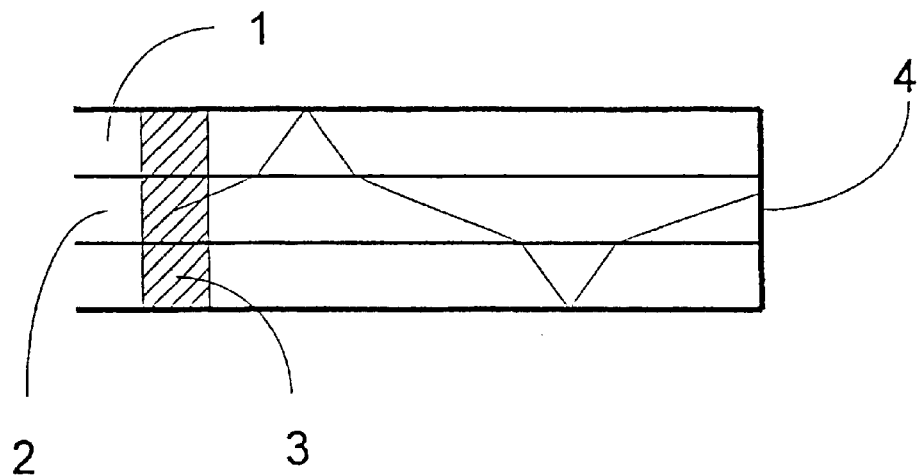
FIG. 1 is a schematic drawing of a light guiding structure in which the RI of the conduit is larger than that of the medium.

In one embodiment of the invention, the refractive index (RI) of the medium containing the fluorescent species is lower than the RI of the conduit containing the medium. Further, the RI of the conduit is larger than the RI of the material surrounding the conduit. This may be illustrated by, e.g., the very common case of an aqueous solution in a fused silica capillary, the capillary being surrounded by, e.g., air or a low RI polymer. In this case, TIR will not take place at the boundary between the medium and the conduit, but at the boundary between the conduit and the surrounding material (and to some extent at the boundary between the conduit and the medium). The absorbance of the surrounding must not be too high, and the reflecting surface to the surrounding must not be too scattering, since this will impair the efficiency of TIR. The light will be guided in both the medium and the conduit. An example of this embodiment is shown in FIG. 1, where fluorescent light emitted from the illumination zone (3) is guided through the conduit (1) and the medium (2) to the light collection end (4).

In a preferred variant of this embodiment, the conduit is made of glass, fused silica, quartz, or an organic polymer. These are very common and practical construction materials for conduits, and do, from an optical point of view, allow for a range of different media, including water and many organic solvents, to be used.

In one aspect of this variant, the conduit has an organic polymer coating. Coating of, e.g., CE capillaries renders the conduits robust enough for most practical handling, and protects the conduits from dirt and scratches. Further, the polymer coating may provide a well-defined optical surface of high quality. Preferably, the conduit is made of fused silica and the coating is a fluoropolymer. The use of fused silica capillaries is well established within CE and high purity fused silica is an excellent optical material. Fluoropolymers do, in general, have a low refractive index, which allows for a high light collection efficiency.

By using a transparent polymer coating of high optical quality, it is not necessary to remove the coating at the illumination zone. The exciting light may simply be directed through the coating and onto the conduit. The used coating must not be highly fluorescent at the employed wavelengths. The most common coating material for CE capillaries is polyimide. This material is fluorescent and not transparent, and has to be removed before excitation. The removal of the coating involves an extra, complicated manufacturing step. After removal of the coating, the capillaries are mechanically very fragile, and the surface of the capillaries is sensitive to dirt and scratches. Small, remaining polyimide particles, may give rise to large amounts of light scattering and background fluorescence.

In another aspect of the present variant, the conduit does not have a coating, but is surrounded by a liquid or a gas. In this way, the coating step may be totally omitted. In CE, the liquid, may or may not be one of the electrolyte solutions. The conduit may be, e.g., the uncoated end of a coated capillary. By using a gas, the lowest possible RI value of the surrounding is obtained. This allows for the most highly efficient light collection by TIR, and for the widest range of conduit materials to be used.

Figure 2:
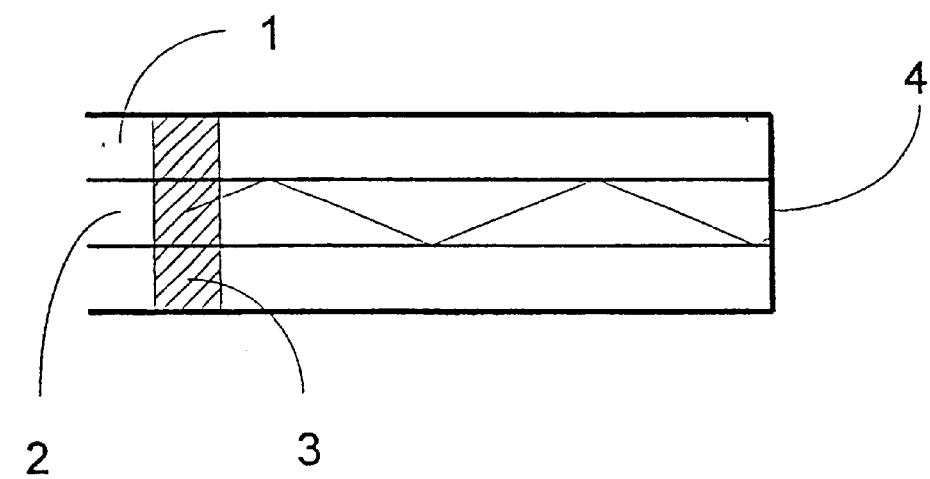
FIG. 2 is a schematic drawing of a light guiding structure in which the RI of the conduit is smaller than that of the medium.

In another embodiment of the invention, the RI of said medium is larger than the RI of the conduit, so that TIR takes place at the boundary between the medium and the conduit. This boundary has to be of good optical quality. In addition, TIR may or may not take place at the boundary between the conduit and the material surrounding the conduit. The first case is analogous to the previously described embodiment. In the second case, the surrounding material should be absorbing, and/or have a higher RI than the conduit. This embodiment allows for other combinations of materials for the conduit and the medium to be used. An example of this embodiment is shown in FIG. 2, where fluorescent light emitted from the illumination zone (3) is guided through the medium (2) to the light collection end (4).

In one variant of this embodiment, the main component of the medium is water, and the conduit is made of an organic polymer, preferably a fluoropolymer or a silicone polymer. This variant makes possible the use of simple, cheap polymer tubing. Since the conduit does not guide the light in this case, the outer shape and dimensions of the conduit are not of primary concern. The conduit may be, e.g., a channel in a piece of polymer material.

In another variant of this embodiment, the main component of the medium is an organic liquid, and the conduit is made of an inorganic material, preferably glass, fused silica, or quartz. This variant allows for a large range of different media to be used, with the only restriction that the RI is higher than that of the conduit. One such conceivable combination is dimethylsulfoxide in a fused silica capillary.

In one embodiment of the invention, the conduit has the shape of a hollow cylinder. This shape is advantageous for efficient transport of light by TIR. In analogy with optical fibers, light can be transported over long distances in cylindrical light guides. The cylindrical case is a very common one; the conduit may be, e.g., a round CE capillary, an LC column, or a piece of LC or FIA tubing. Further, it is simple in practice to design systems with cylindrical light guides.

For this embodiment, it is straightforward to calculate the light collection efficiency of the device. The equation for the numerical aperture (N.A.) of optical fibers is:

$$N.A. = (n_{core}^2 - n_{coating}^2)^{0.5}$$

Thus, as an example, realising that other values of N.A. may be obtained for other combinations of materials, for a light guide with core RI equal to 1.36 (e.g., a water based buffer or hydrogel) and coating RI equal to 1.31 (e.g., a fluoropolymer), the N.A. is 0.37, equal to a high N.A. optical fiber. Obviously, the invented device may yield an adequate light collection efficiency. Further, such a value of N.A. is compatible with common collecting optics, like, e.g., condenser lenses. Collecting optics with equal or higher N.A. have been reported in some on-column, orthogonal and confocal setups. However, light leaving a cylindrical silica capillary through the cylindrical outer surface will diverge heavily when passing the silica/air interface, so the actual light collection efficiency of such systems may be significantly lower.

In a preferred variant of this embodiment, the inner diameter of the cylinder is less than or equal to 500 $\mu$m, or more preferably less than or equal to 100 $\mu$m. This is the case for, e.g., capillary columns and capillary tubing for micro-LC and for CE. The present invention provides a means of efficiently collecting, guiding, and detecting light even for very narrow-bore tubing.

Figure 3:
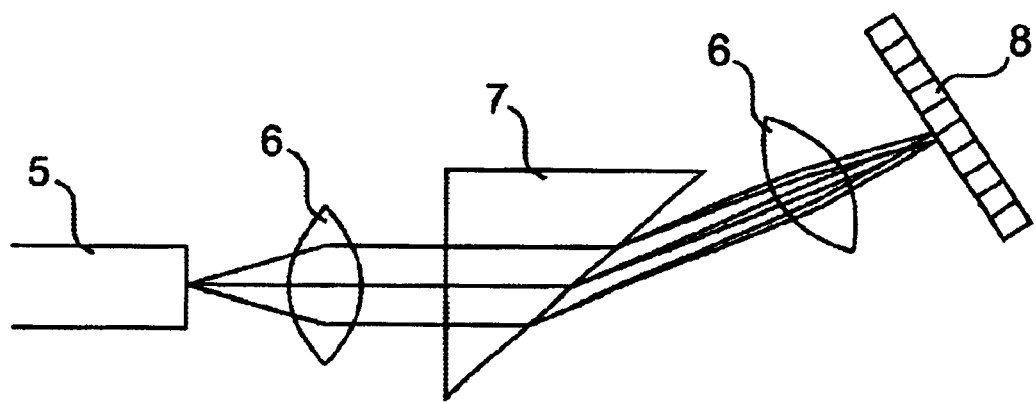
FIG. 3 is a schematic drawing of spectral resolution of light collected from a capillary.

In one embodiment of the invention, the light that is collected from the end of said structure is spectrally resolved. Spectral resolution enhances the versatility and the selectivity of the device. Preferably, spectral resolution is performed by means of one or several prisms, gratings, or optical filters. It may be advantageous to first collect and collimate the light leaving the light guiding structure by means of focusing optics. Primary light may be blocked by, e.g., interference or low pass filters. An example of this embodiment is shown in FIG. 3, where light exiting a capillary (5) is collected by a lens (6) and spectrally dispersed by a prism (7) before being focused by a second lens (6) onto the light detector (8).

In one embodiment of the invention, the light that is collected from the end of said structure is detected by an imaging light detector, preferably a CTD or a photodiode array. An imaging detector consists of several detector pixels, and is able to render an image of the geometrical distribution of light. By using such a detector, an image of light leaving the light guiding structure at different positions and angles may be obtained. This may be advantageous in some cases, e.g., for rejecting stray light or when using a multitude of light guiding structures.

In one embodiment of the invention, the light that is collected from the end of said structure is spatially resolved, preferably by use of an aperture or by rejecting part of a detected image. An aperture is commonly used within photography or microscopy to perform spatially resolved detection of light. An imaging detector may perform the same task: only those pixels containing the desired information is read out or stored in memory, while the signal from other pixels is rejected. Of course, spatial resolution may also be accomplished by selecting the appropriate size and position of a non-imaging detector (e.g., a single photodiode), but this may often prove impractical.

Figure 4:
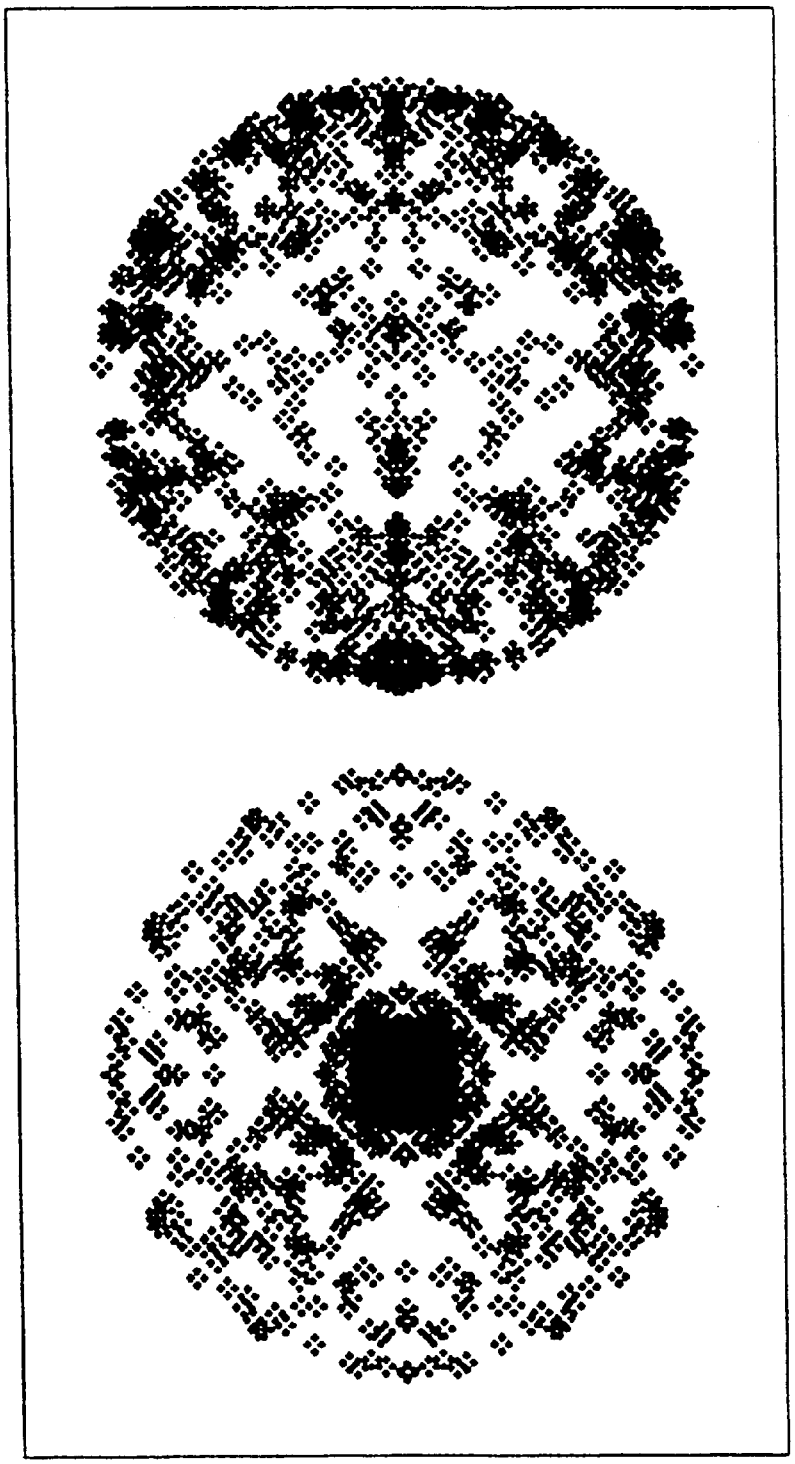
FIG. 4 is a ray-tracing diagram for light emanating from different locations in a light guiding structure.

An example of the beneficial influence of this embodiment is shown by the ray-tracing calculation depicted in FIG. 4. The calculation is made for a cylindrical conduit with outer diameter 375 µm, inner diameter 100 µm, RI 1.46, filled with a medium of RI 1.36 in the inner channel, and surrounded by air. In FIG. 4a, a ray-tracing calculation for a number of light rays emanating from the center of the structure, as is the case for emission of fluorescent light in the inner channel, was performed. The figure, showing a cross section of the capillary, illustrates the distribution of internally reflected light rays within the capillary at some distance away from the illumination zone. The rays travel mainly close to the center of the capillary, and the light intensity is especially high within the gel-filled inner channel. FIG. 4b shows the same calculation for a number of rays emanating from a point close to the outer surface of the structure, as is the case for scattering of primary light hitting the outer surface. The rays travel mainly close to the circumference of the capillary. By imaging the end of the structure onto an imaging detector, and selecting only pixels covering the center region, the scattered light may to a large extent be rejected, while the fluorescent light is efficiently detected. Clearly, the present invention provides a means of efficiently separating stray light, emanating from regions outside of the medium, from fluorescent light, emanating from inside the medium, by spatial resolution, using the set-up in the example, or one of a multitude of other setups.

In one embodiment of the invention, the exciting light is light from a laser. Lasers possess the advantages of high intensity and well-defined excitation wavelengths. Further, laser light may easily be focused down to very small dimensions, which is advantageous in connection with narrow capillaries. For the purposes of the present invention, the highly collimated light from lasers provide an extra advantage: the illumination geometry may easily be controlled, and the amount of primary light coupling to the light guide through TIR may be kept very low.

Figure 5:
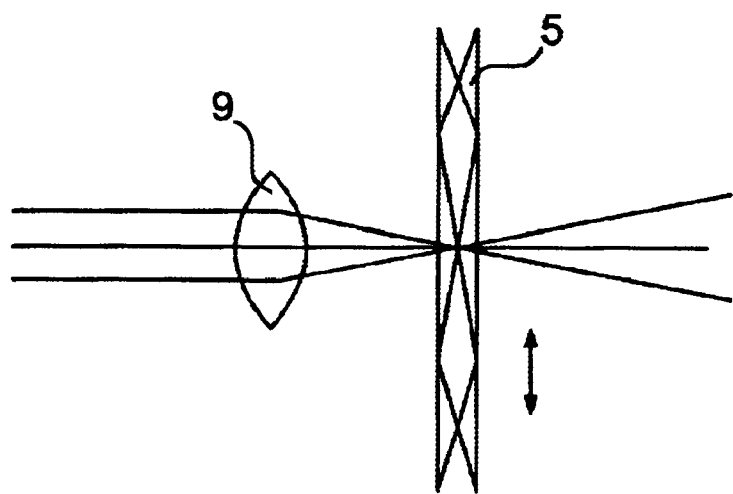
FIG. 5 is a schematic drawing of exciting light being focused before reaching a capillary.

In one embodiment of the invention, the exciting light is focused in a direction parallel to the guiding direction of the emitted fluorescent light along said light guiding structure. Preferably, the width of the exciting beam (in the said direction) should be less than 500 µm, and more preferably less than 200 µm. For a discrete capillary, e.g., the light is focused in the axial direction of the capillary, which is the same direction in which light is guided. In most cases, this direction coincides with the transport direction of the sample in the conduit. A small axial excitation length and a small excitation volume are important in, e.g., CE, where the separation efficiency is high and the analyte bands are very narrow. In addition, the exciting light may, or may not, be focused in an orthogonal direction to said direction. For one, discrete capillary, e.g., the light may be focused in two directions by means of an ordinary, round lens. For a multitude of capillaries or other structures, the light may be focused in only one direction (line-focused) by means of a cylindrical lens. An example of this embodiment is shown in FIG. 5, where the exciting light is focused by a lens (9) before reaching the capillary (5). The double headed arrow shows the direction in which light is guided in the capillary.

In one embodiment of the invention, the angle between the propagation direction of the exciting light and the guiding direction of the emitted fluorescent light along said light guiding structure is large enough, preferably orthogonal or nearly orthogonal, to prevent any non-scattered component of the exciting light to be optically coupled into the guiding direction of the light guiding structure by total internal reflection. In order to keep the level of stray light low, the amount of primary, exciting light coupling into the light guide by means of TIR should be kept as low as possible. The obvious way to achieve this is to keep the angle a for the exciting light as low as possible, which equals orthogonal or nearly orthogonal illumination. For a well-collimated beam and a low angle α, it is (ignoring light scattering) possible to keep the amount of TIR coupled primary light extremely low.

Figure 6:
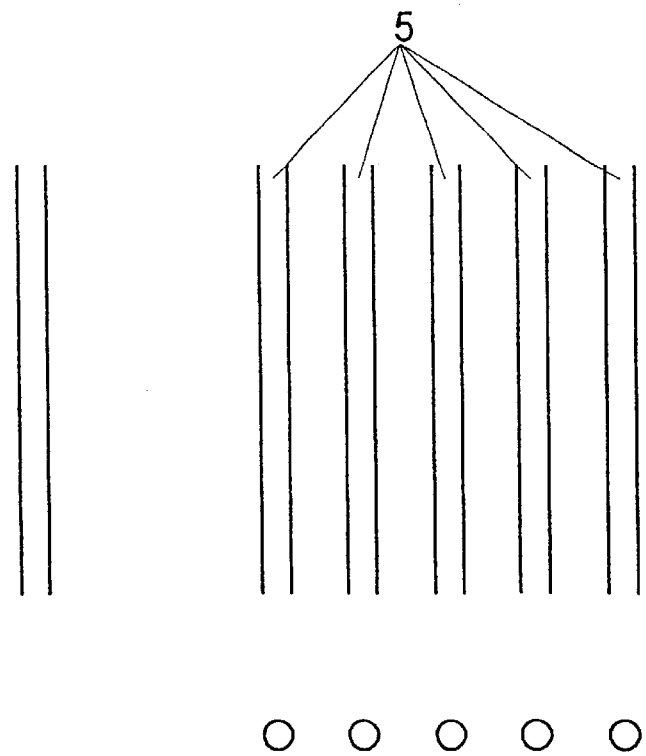
FIG. 6 is a schematic drawing of a number of capillaries arranged in the form of a planar array.

In one embodiment of the invention, a multitude of said structures are arranged in the form of an array, preferably a planar or nearly planar array, at the illumination zone. This may be the case, e.g., for multiplexed CE. Since light is guided by TIR within each separate structure, the present invention is well suited for array detection. The present invention has several advantages with respect to multiplexed detection, as will be further discussed below. An example of this embodiment is found in FIG. 6, where a number of capillaries (5) arranged in the form of a planar array are shown from different views.

Figure 7:
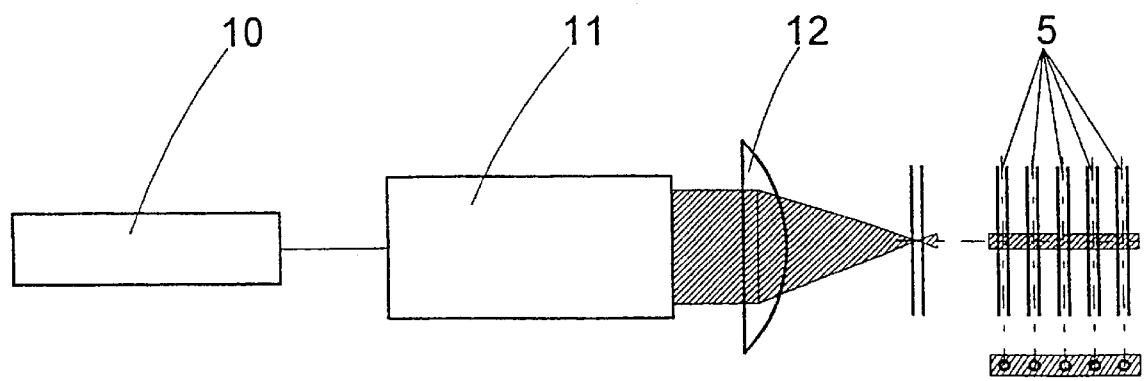
FIG. 7 is a schematic drawing of light being spatially dispersed before reaching a planar array of capillaries.

In one variant of this embodiment, the exciting light is spatially dispersed across said array. This variant is especially advantageous in connection with planar arrays. The direction of the exciting light is orthogonal or nearly orthogonal to the planar array. The light is geometrically spread out across the array, preferably by means of one or several lenses, a beam expander, or a diffractive beam shaper. The light may, or may not, be focused in a direction orthogonal to the dispersion direction, e.g., by means of a cylindrical lens. This illumination geometry provides a very simple and clean illumination: the exciting light passes very few optical surfaces, resulting in a low amount of scattering. In contrast hereto, exciting light travelling in the plane of the planar array will hit the multitude of structures in a subsequent manner, and will pass many optical surfaces, giving rise to a large amount of scattering. Further, even though laser beams can be tightly focused, laser beams are divergent. The more tightly focused the beam is, the more divergent it becomes. In order to keep the axial excitation length or the excitation volume small, it is essential to keep the beam tightly focused, and so it is essential to keep the interaction length between the beam and the multitude of structures small. This is achieved when the exciting light is orthogonal or nearly orthogonal to the planar array, but not when the beam hits the multitude of structures in a subsequent manner. An example of this variant is shown in FIG. 7, where light from a laser (10) is spatially dispersed in two dimensions by means of a beam expander (11) an focused in one dimension by a cylindrical lens (12) before reaching the planar array of capillaries (5). The hatched areas show the approximate extent of the laser beam from different views.

In another variant of this embodiment, the exciting light is scanned across said array. Again, the direction of the exciting light may be orthogonal or nearly orthogonal to a planar array. In this way, the exciting light is shared between the different structures in time rather than in space. The light is preferably focused in two directions by means of one or several ordinary, round lenses. Either the light beam may be scanned, or the array may be scanned. One alternative is to place the multitude of structures in a circular array, and to rotate the optics inside this array. This variant has the same advantages as the previous one. It is also possible to use combinations of these two variants, e.g., a scanning system in combination with a diffractive beam splitter.

Figure 8:
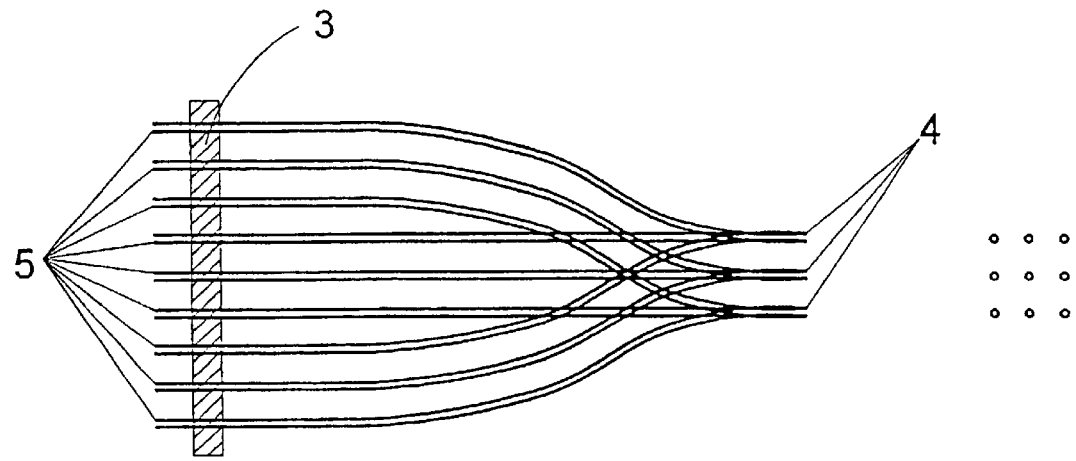
FIG. 8 is a schematic drawing of a planar array of capillaries being rearranged into a square array at the light collection ends.

In one embodiment of the invention, the light collection ends of said array, preferably planar or nearly planar, of structures are geometrically rearranged in a way that is advantageous for the efficient collection of light, preferably in the form of a two dimensional array. Fundamental optical constraints limit the efficient collection of light from an extended planar array of, e.g., capillary ends. High numerical aperture lenses collect light efficiently from a localised region; low numerical aperture lenses have poorer collection efficiency but a wider field-of-view. By rearranging the ends of the structures, e.g., the capillaries, in a more compact form, e.g., a square, rectangular, or other polyhedral array, it becomes possible to collect light from a large number of structures with a high efficiency. As an example, a densely packed planar array of 100 CE capillaries with an outer diameter of 0.5 mm is 50 mm wide, and causes difficulties with respect to light collection. On the other hand, if the capillary ends are rearranged into a densely packed square array, the largest array dimension becomes only 5 mm, which makes light collection significantly easier. By using the light guiding principle of the present invention, it is possible to rearrange the geometrical set-up of the multitude of structures in between the illumination zone and the light collection ends. A multitude of, e.g., fused silica capillaries, may easily be rearranged from a planar array to a square array over a distance of a few centimeters by slightly bending the capillaries. Such slight bending does not significantly affect the light guiding ability of the capillaries. Arranging the multitude of structures into a two dimensional array already at the illumination zone will cause problems with respect to the focusing of laser beams over extended distances and with respect to light scattering caused by the exciting light hitting many optical surfaces, as discussed above. An example of this embodiment is shown in FIG. 8, where a number of capillaries (5) are arranged in a planar array at the illumination zone (3), but rearranged into a square array at the light collection ends (4).

It may be noted, that dense packing of many capillaries generally causes band broadening due to inefficient dissipation of the evolved Joule heat in CE separations. In the present case however, the capillaries are densely packed only after the point of excitation, so Joule heating will not impair the measured separation efficiency.

Figure 9:
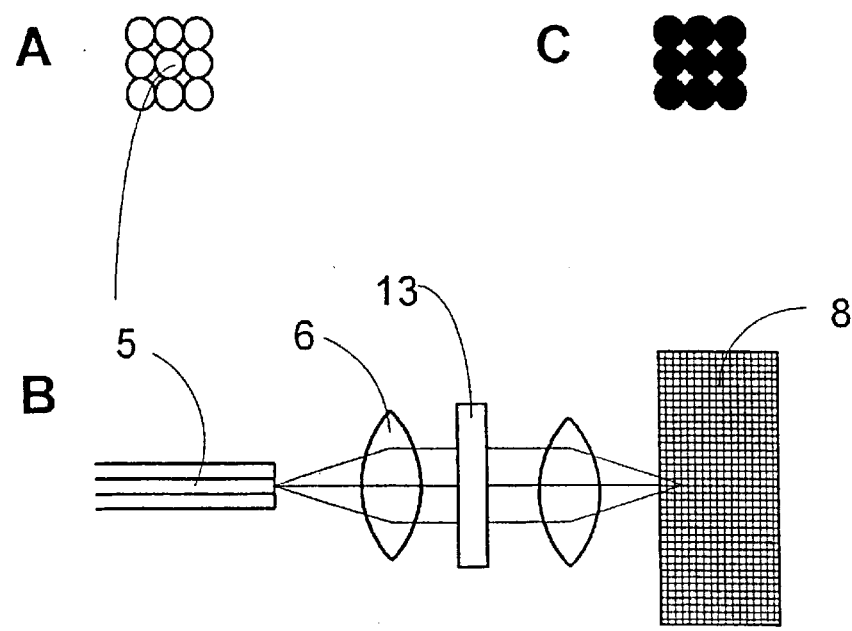
FIG. 9 is a schematic drawing of a densely packed capillary array being imaged onto a light detector.

In one variant of this embodiment, said two dimensional array is densely packed, and the collected light is spectrally resolved by means of one or several optical filters. If a densely packed two dimensional array is imaged onto the surface of an imaging detector, the image may occupy a considerable continuous area on the surface, and there may not be enough space left on the surface for wavelength dispersion of individual structures in one dimension by means of, e.g., a prism or a grating. In this case, spectral resolution may be obtained by means of one or several filters, e.g., one or several high or low pass filters or interference filters. The filters may be arranged, e.g., as a train of filters [Kheterpal, I. et al., Electrophoresis, 1996, 17, 1852–59] or on a rotating filter wheel. An example of this variant is shown in FIG. 9. FIG. 9a shows a number of capillaries (5) that are densely packed. FIG. 9b shows light from the capillaries being collected by a lens (6) and passed through a filter (13) on a rotating filter wheel, before being imaged on the detector (8). FIG. 9c shows the image of the capillary array on the detector at one defined point of time.

Figure 10:
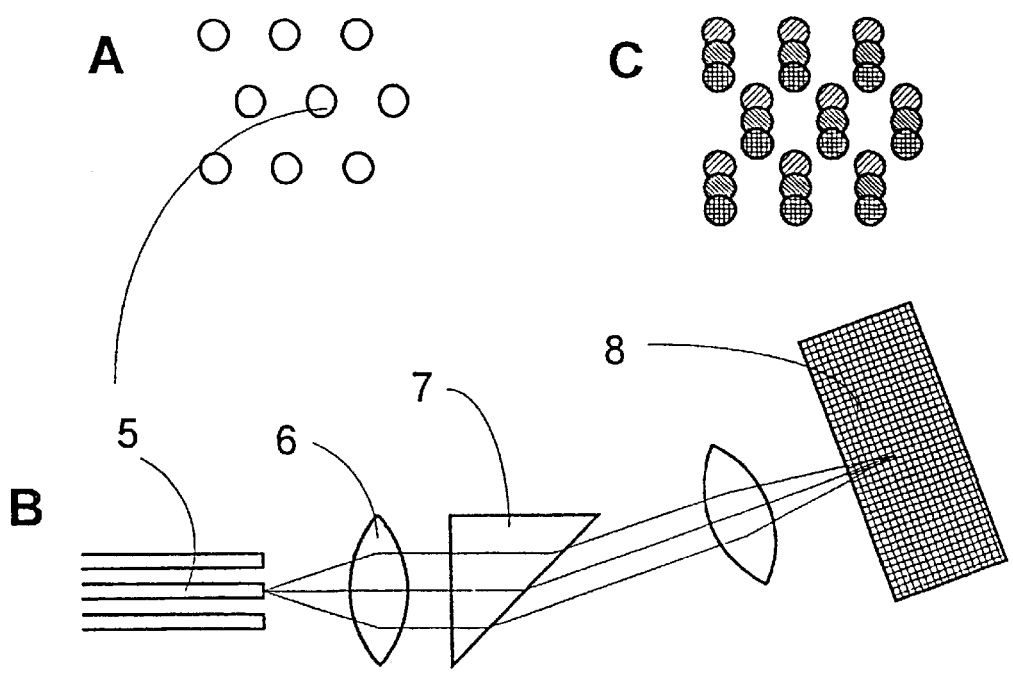
FIG. 10 is a schematic drawing of a sparsely packed capillary array being imaged onto a light detector.

In another variant of this embodiment, said two dimensional array is sparse enough to allow for the collected light to be spectrally resolved onto the surface of an imaging detector by means of one or several prisms or gratings. The image on the surface of an imaging detector becomes sparse enough, so that there is space in between the image of individual structures for spectral resolution in one direction. An example of this variant is shown in FIG. 10. FIG. 10a shows a number of capillaries (5) that are sparsely packed. FIG. 10b shows light from the capillaries being collected by a lens (6) and passed through a prism (7) before being imaged on the detector (8). FIG. 10c shows the spectrally resolved image of the capillary array on the detector. The round images of individual capillaries are stretched out due imaging of different colours on different spots on the detector.

In one embodiment of the invention, using a multitude of said structures, the individual structures may be identified by coupling light by total internal reflection into the structures at some point other than the light collection end, and collecting said light from the light collection ends of said structures. If, e.g., a large number of CE capillaries are bundled together and imaged at the light collection end, it may be difficult to identify which injection end belongs to a specific imaged light collection end. However, by shining light, e.g., from a light emitting diode, onto each capillary, on at a time, at the injection end, letting the light be guided to the light collection end by TIR, and monitoring the image on the detector, this problem may be solved. Thus, it becomes possible to bundle a large number of capillaries together in a non-systematic and random way, and to identify the individual capillaries afterwards.

In addition to what is explained above, it is obvious that the present invented device, as compared to the on-column orthogonal optical set-up, provides a simple and efficient means of obtaining high light collection efficiency and of separating primary light and stray light from emitted fluorescent light, especially in connection with multiplexed detection. In comparison with the confocal microscope, the focal depth is not critical, and so the robustness with respect to mechanical tolerances, optical alignment, and, e.g., vibrations is significantly higher. For multiplexed detection, no moving parts are necessary for the present invention. In comparison with the sheath flow cell, the present device does not put as high demands on the sophistication, control, and tolerances of the flow system, and so offers a significantly higher degree of robustness. Further, the present device offers a simple solution to the problem of illumination of a multitude of capillaries.

Internally reflected light may, in principle, be decoupled from the structure through its circumference by means of an external optical decoupler, and collected before reaching the end of the structure. Such a decoupler may be, e.g., an optical fiber pigtailed onto the structure. However, such decoupling has several drawbacks. The structure must not be coated, or the coating has to be removed at the decoupling point. The RI of the medium must not be higher than that of the conduit. Optical decoupling does not provide for any means of stray light rejection like, e.g., the sheath flow cell and the confocal microscope do. Since spatial information is lost on decoupling, any rejection of stray light by spatial resolution is impossible. Rather, since stray light may travel mainly close to the circumference of the structure and fluorescent light mainly close the center, decoupling through the circumference of the structure may lead to enrichment of stray light. Further, optical alignment of a large number of decouplers to a multitude of structures involves a huge amount of work, and the decouplers may occupy a considerable space, making this arrangement less well suited for multiplexed detection.

There are several applications of the invented device. A few examples will be given, but the applicability is not limited to these examples, and other applications will be obvious to the skilled person. The device may be used for the detection of species with native fluorescence as well as species labelled with one or several fluorophores. Native fluorescence in the UV region is exhibited, e.g., by the amino acids tryptophan and tyrosine. Labelling with two fluorophores may refer, e.g., to the use of energy transfer fluorophores, with one donating and one accepting fluorophore [Ju, J. et al., Nature Medicine 1996, 2, 246–49]. The device may be used for detection in connection with any method involving the transportation of said species across the illumination zone within said conduit. Such methods are very common within chemical and biochemical analysis. The sample may, e.g., be transported within a length of capillary tubing by means of pressure, electroosmotic flow, or migration in an electric field. The device may, e.g., be used for detection in connection with capillary electrophoresis, including capillary zone electrophoresis, capillary gel electrophoresis, micellar electrokinetic capillary chromatography, and capillary isoelectric focusing, capillary electrochromatography, liquid chromatography, or flow injection analysis. The device may be used for detection in connection with nucleic acid analysis, e.g., in connection with DNA sequencing. One application of special interest is high throughput DNA sequencing by CE in arrays of capillaries.

The method of the invention will now be illustrated by the following, non-limiting examples.

EXAMPLES

Figure 11:
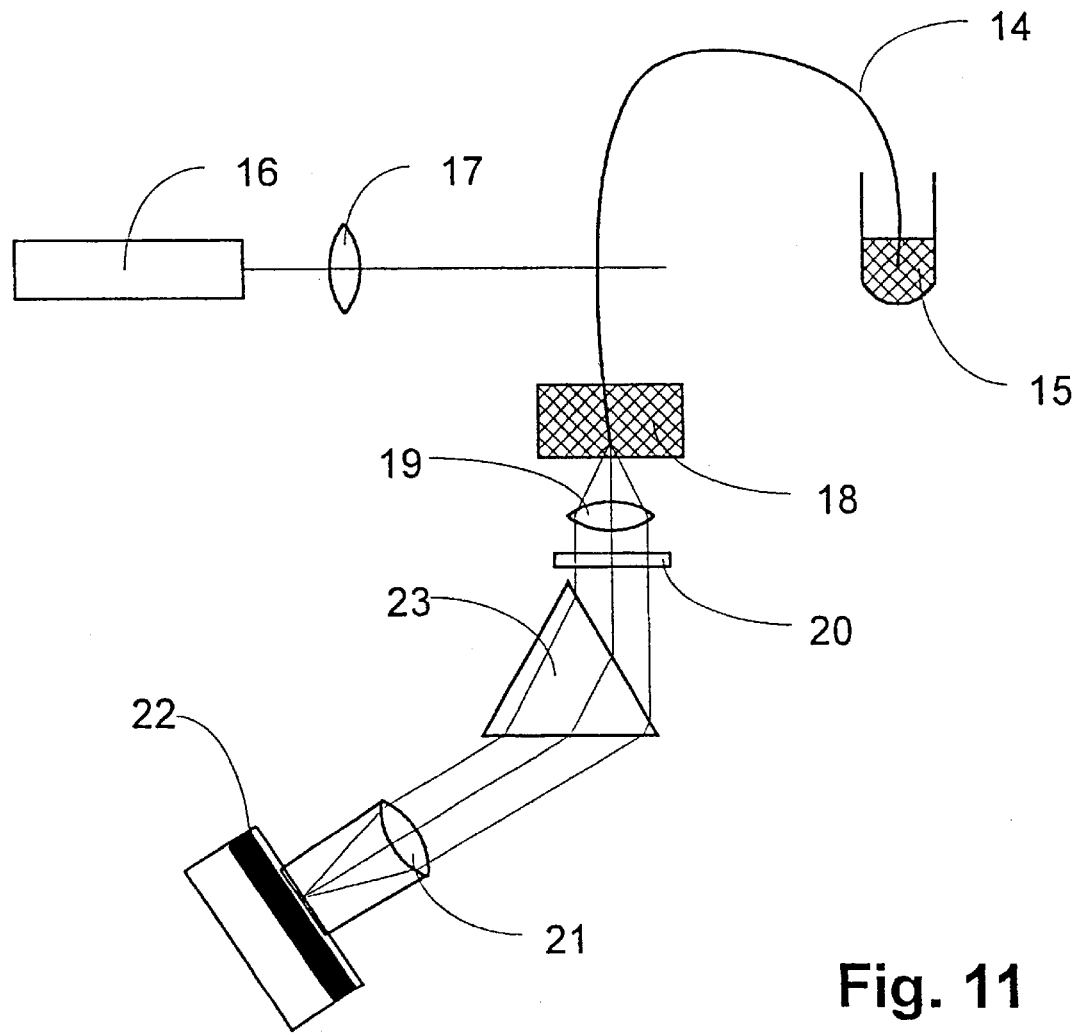
FIG. 11 is a schematic drawing of the device used in the Examples.

The device used in the examples is shown in FIG. 11.

In all examples, fluoropolymer coated cylindrical fused silica capillaries (14) with i.d. 100 $\mu$m and o.d. 375 $\mu$m (TSU100375, Polymicro, Phoenix, Ariz., USA) were used. The injection end of the capillary was placed in a liquid filled chamber (15). Light from an argon ion laser (16) (2013-150ML, Uniphase, San Jose, Calif., USA), emitting mainly at 488 and 514 nm, was focused by a lens (17) and illuminated the capillary at 90°. The laser power hitting the capillary was estimated to about 3 mW. The polymer coating was not removed at the illumination zone. The axial illumination length of the laser in the capillary was estimated to 25 $\mu$m, and so the detection volume was estimated to 0.2 nl. Light was guided about 5 cm to the end of the capillary, which was placed in a liquid filled chamber (18). Light exiting the end of the capillary was collected, end-on, by a condenser lens (19) (063098, Spindler & Hoyer, Göttingen, Germany). Primary light was filtered by one or two low pass glass filters (20) (OG 530, Schott Glaswerke, Mainz, Germany). The light was collected by a 50 mm camera objective (21) (Series E 1/1.8, Nikon, Tokyo, Japan) onto the surface of a CCD (22) (TE/CCD-1024-TKB/1, Princeton Instruments, Trenton, N.J., USA). In some experiments, a prism (23) (336675, Spindler & Hoyer) was placed in between the glass filter and the camera objective to obtain spectral resolution. The collected images were stored and evaluated by means of WinView software (Princeton Instruments) on an IBM-compatible PC.

Example 1

Figure 12:
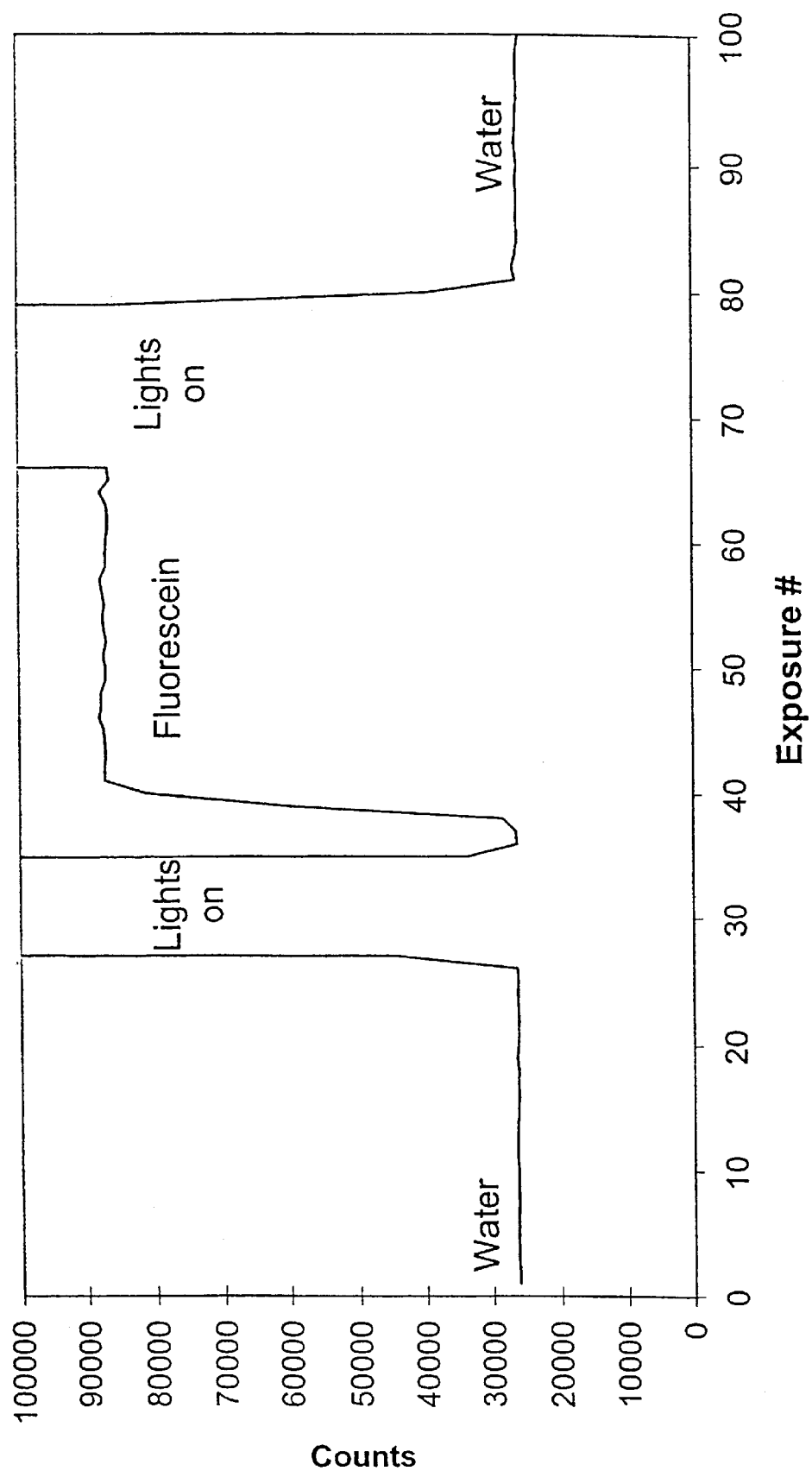
FIG. 12 is a trace of the fluorescent signal recorded during the pumping of a fluorescein solution through a capillary.

In this example, the prism (23) was left out of the optical setup, and the collected light was not spectrally resolved. First, water was pumped continuously through the capillary for a few minutes by means of pressurised air. Then, a 0.7 nM solution of fluorescein (16630-8, Aldrich, St. Louis, Miss. USA) in water was pumped in the same way. The exposure time of the camera was 1 s. The recorded trace is shown in FIG. 12. The obtained signal was calculated as the difference between the number of counts, summed over a number of pixels, for fluorescein and water, respectively. The noise was calculated as the standard deviation of the water baseline. The concentration detection limit (taken as 3× the noise) was 2.7 pM, and the mass detection limit was 550 ymoles. The example shows the efficient collection and detection of fluorescent light, and demonstrates the excellent detection limit obtained with the device.

Figure 13:
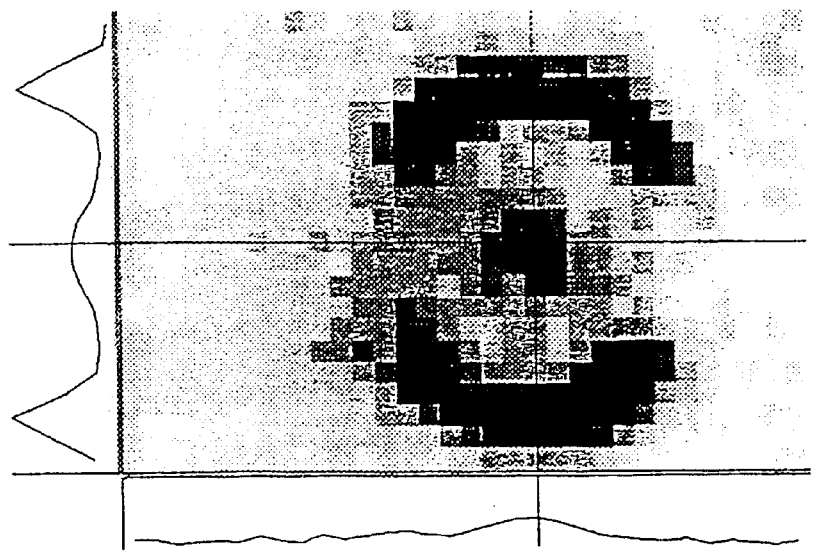
FIG. 13 shows images of the light collection end of a capillary during pumping of water and fluorescein, respectively.
Figure 13:
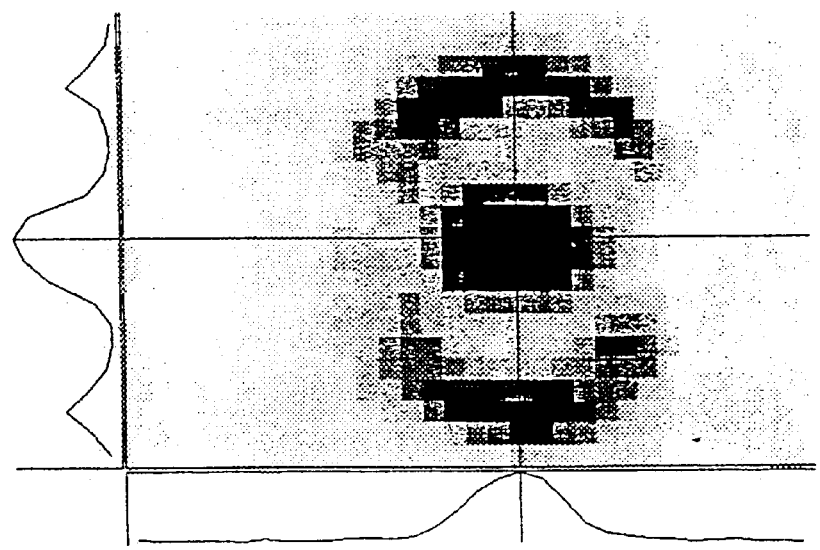

In FIG. 13, images of the end of a capillary are shown. FIG. 13a shows the image for pure water. The main feature is a circle of light close to the circumference of the column, due to light scattering at the outer surface. FIG. 13b shows the image for fluorescein. The main feature is an approximately Gaussian light peak in the center of the column, due to emission of fluorescent light. The peak is superimposed on the ring-shaped background. Clearly, by only reading out pixels close to the center, it is possible to reject stray light through spatial filtering.

Example 2

Figure 14:
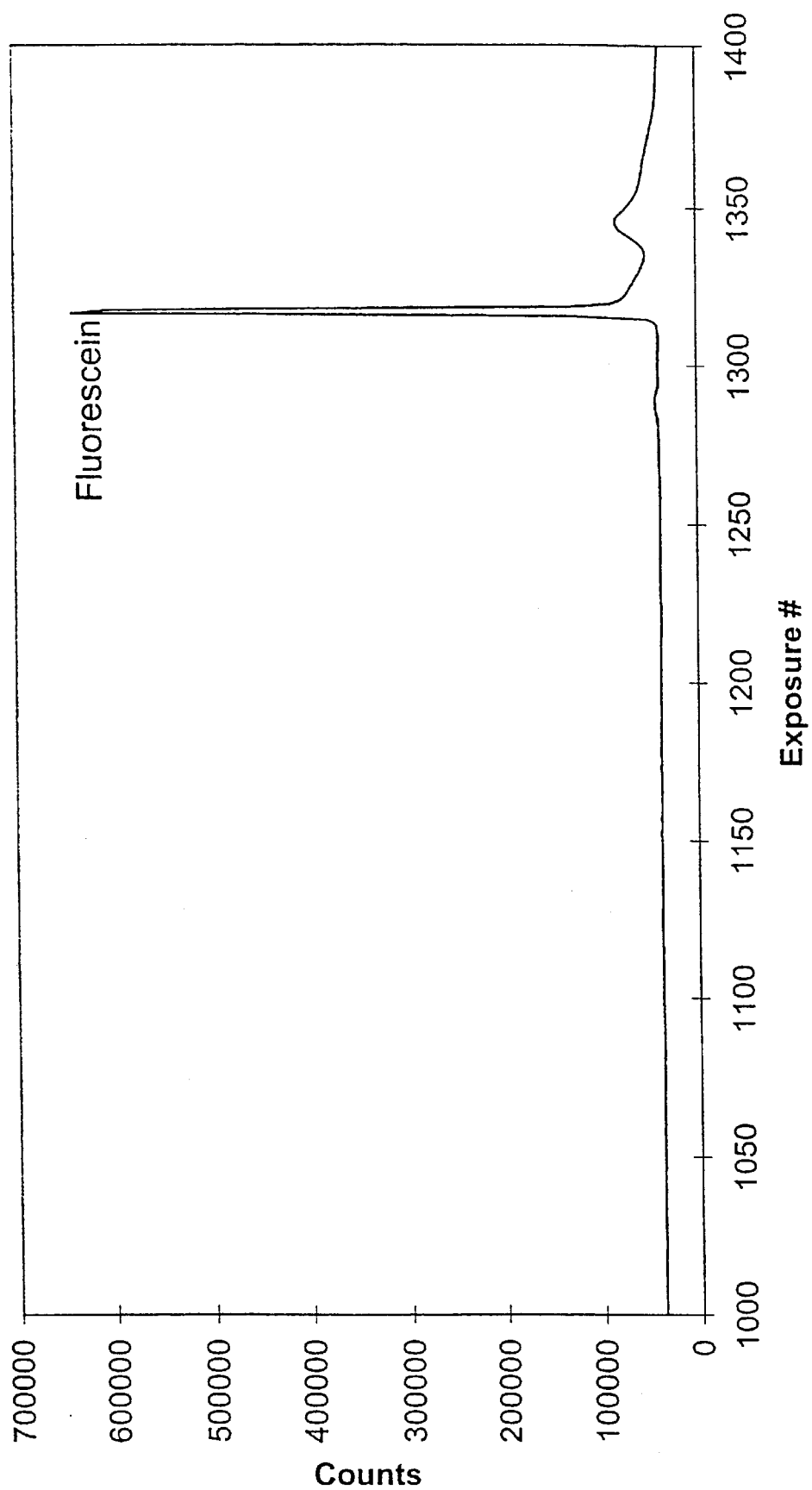
FIG. 14 is an electropherogram of a fluorescein injection.

In this example, the prism (23) was used. The column was filled with a crosslinked hydrogel (poly (dimethylacrylamide), 7% T, 4% C). The length of the capillary from the injection end to the illumination zone was about 30 cm. The liquid chambers were filled with a buffer consisting of 0.1 M Tris, 0.1 M borate, 2 mM EDTA, and 7 M urea. An 0.084 nM solution of fluorescein (F-1130, Molecular Probes, Eugene, Oreg., USA) in water was electrokinetically injected at 4 kV for 20 seconds, and electrophoresed at 5 kV. The exposure time was 0.6 s. FIG. 14 shows part of the electropherogram. The concentration detection limit for the fluorescein peak was 70 fM. Again, the example demonstrates the excellent detectability of the device.

Example 3

Figure 15:
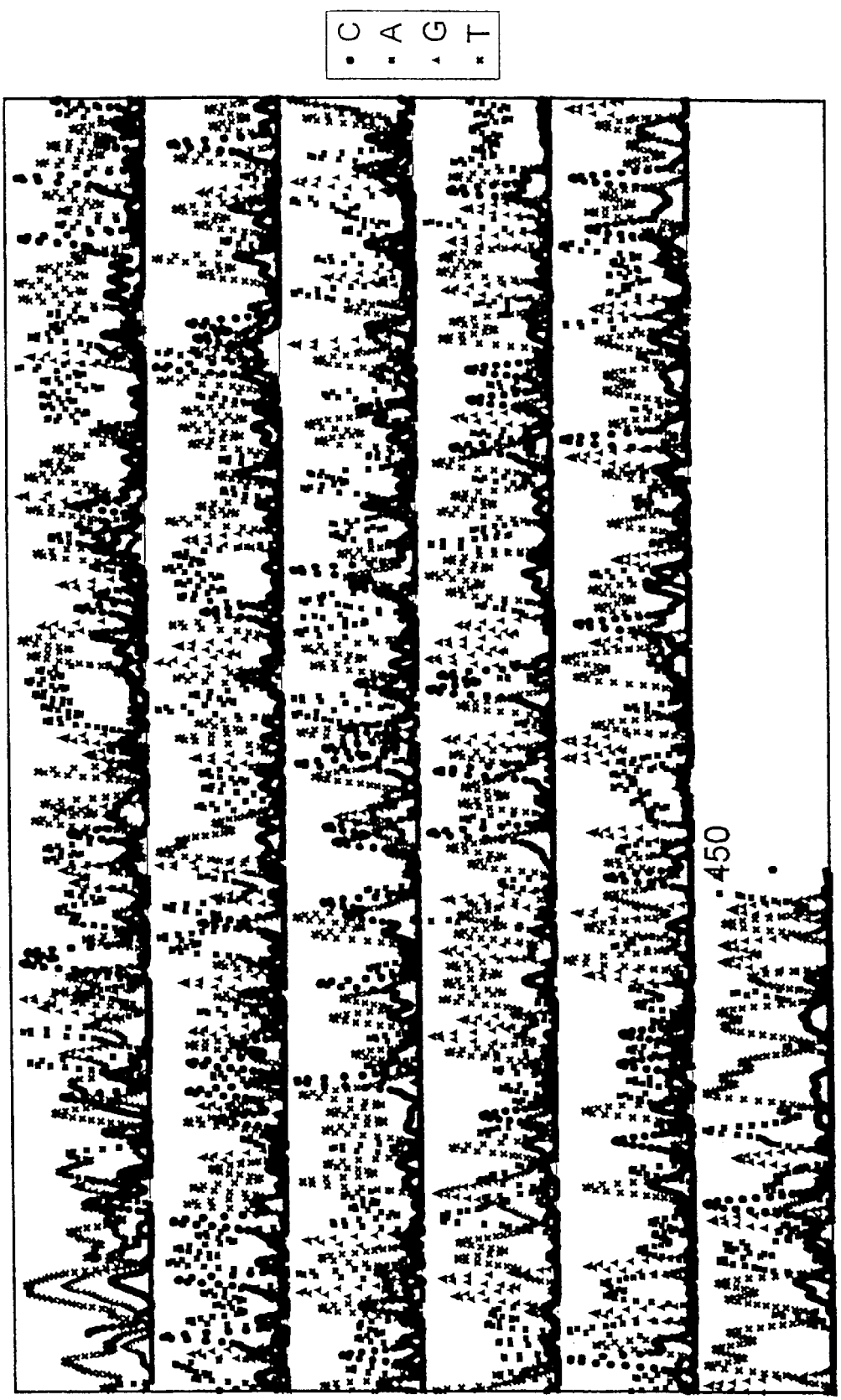
FIG. 15 is a DNA sequence obtained with the device of FIG. 11.

The same optical set-up, column, and electrophoresis conditions as in the previous example were used. The sample was a cycle sequencing DNA sample, precipitated in ethanol and dissolved in water. The primers were labelled with four different fluorophores (FAM, JOE, TAMRA, ROX) (Genpak, Brighton, UK) and pooled together before the analysis. The individual pixels of the CCD-chip were binned into larger superpixels. The spectrum of each data point was recorded as a ten superpixel spectrum in the approximate region 520–670 nm. Wavelength calibration was performed by shining light from light emitting diodes of known wavelength onto the injection end, and recording the obtained spectra. The sequence was evaluated by identifying a number of pure peaks of each base from the known sequence, and taking the spectrum for these peaks as representative of the pure bases. Then, the base composition of the remainder of the electropherogram was calculated by mathematical fitting of these calibration spectra to each of the data points. FIG. 15 shows the so obtained base sequence. The base calling accuracy is estimated to 96–98% in the region 40–450 bases. The example shows the excellent detectability, the negligible detector band broadening contribution, and the wavelength resolution ability of the device, and clearly demonstrates the applicability to DNA sequencing.

The invention is, of course, not restricted to the aspects, embodiments, and variants specifically described above, or to the specific examples, but many changes and modifications may be made without departing from the general inventive concept as defined in the following claims.

What is claimed is:

1. A device for detection of one or several fluorescent species, said species being contained in a medium, said medium being contained in a conduit, said device comprising a means of exciting the fluorescent species by light in an illumination zone, and means of collection and detection of fluorescent light emitted by said fluorescent species, said medium and conduit making up a structure that is transparent to the exciting light and to fluorescent light emitted by said fluorescent species, and said device comprising several such structures, characterised in that the refractive index of said medium is larger than that of said conduit or characterised in that said conduit is made of fused silica, quartz, or an organic polymer which conduit has an external organic polymer coating which has a refractive index lower than that of the fused silica, quartz, or organic polymer and which coating is transparent to the exciting light, so that at least part of the emitted fluorescent light is guided away from the illumination zone by total internal reflection in said structures and collected from one end of said structures.

2. The device according to claim 1, wherein said conduit is made of fused silica and has a fluoropolymer coating.

3. The device according to claim 1, wherein the main component of said medium is water, and that said conduit is made of an organic polymer.

4. The device according to claim 3, wherein the organic polymer is a fluoropolymer or a silicone polymer.

5. The device according to claim 1, wherein the main component of said medium is an organic liquid, and said conduit is made of glass, fused silica, or quartz.

6. The device according to claim 1, wherein a multitude of said structures are arranged in the form of a planar array, at the illumination zone.

7. The device according to claim 6, wherein the exciting light is spatially dispersed across said array by means of one or several lenses, a beam expander, or a diffractive beam shaper.

8. The device according to claim 6, wherein the exciting light is scanned across said array.

9. A device according to claim 6, wherein the light collection ends of said array are geometrically rearranged in the form of a two dimensional array.

10. The device according to claim 1, wherein the light that is collected from the end of said structure is detected by an imaging light detector.

11. The device according to claim 10, wherein the imaging light detector is a charge transfer device or a photodiode array.

12. The device according to claim 1, wherein the device additionally comprises means for spectral resolution of the light that is collected from the end of said structure.

13. The device according to claim 12, wherein the means for spectral resolution Is one or several prisms, gratings, or optical filters.

14. The device according to claim 9, wherein the collected light is spectrally resolved by means of one or several optical filters.

15. The device according to claim 9, wherein said two dimensional array is sparse enough to allow for the collected light to be spectrally resolved onto the surface of an imaging detector by means of one or several prisms or gratings.

16. The device according to claim 1, additionally comprising a means for spatial resolution of the light that is collected from the end of said structure.

17. The device according to claim 16 wherein the light is spatially resolved by use of an aperture or by rejecting part of a detected image.

18. The device according to claim 1, wherein the exciting light is focused in a direction parallel to the guiding direction of the emitted fluorescent light along said light guiding structure.

19. The device according to claim 1, wherein the exciting light is light from a laser.

20. The device according to claim 1, wherein the angle between the propagation direction of the exciting light and the guiding direction of the emitted fluorescent light along said light guiding structure is orthogonal, to prevent any non-scattered component of the exciting light to be optically coupled into the guiding direction of the light guiding structure by total internal reflection.

21. The device according to claim 1, wherein the distance between the illumination zone and the light collection end of said structure is large enough to allow light rays emanating from the illumination zone, which do not fulfil the conditions for total internal reflection, to be efficiently transmitted out of the light guiding part of said structure before reaching the light collection end.

22. The device according to claim 21, wherein the distance between the illumination zone and the light collection end of said structure is at least four times, at least eight times, or at least sixteen times, larger than the largest cross sectional dimension of the light guiding part of said structure.

23. The device according to claim 1 wherein said conduit has the shape of a hollow cylinder.

24. The device according to claim 23, wherein the inner diameter of said cylinder is less than or equal to 500 $\mu$m, or less than or equal to 100 $\mu$m.

25. Device according to claim 1 comprising means for identifying individual structures by coupling light by total internal reflection into the structures at some point other than the light collection end and collecting said light from the light collection ends of said structures.

26. Use of the device according to claim 1 for detection of species with native fluorescence or species labelled with one or several fluorophores.

27. Use of the device according to claim 1 for detection in connection with any method involving the transportation of said species across the illumination zone within said conduit.

28. Use of the device according to claim 1 for detection in connection with capillary electrophoresis, including capillary zone electrophoresis, capillary gel electrophoresis, micellar electrokinetic capillary chromatography, and capillary isoelectric focusing, capillary electrochromatography, liquid chromatography, or flow injection analysis.

29. Use of the device according to claim 1 for detection in connection with nucleic acid analysis.

30. Use of the device according to claim 1 for detection in connection with DNA sequencing.

* * * * *